(12) United States Patent
Koenig et al.

(10) Patent No.: US 11,311,429 B2
(45) Date of Patent: Apr. 26, 2022

(54) METHODS AND PRODUCTS FOR DYNAMIC CONTROL OF ENVIRONMENTS BY SELECTIVE METABOLIC FUNCTION OF MICROBES

(71) Applicant: Kimberly-Clark Worldwide, Inc., Neenah, WI (US)

(72) Inventors: David W. Koenig, Menasha, WI (US); Jonathan Hofmekler, Sandy Springs, GA (US); Lindsay A. Peed, Norcross, GA (US); Jeffery R. Seidling, Neenah, WI (US); Scott W. Wenzel, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 17/426,910

(22) PCT Filed: Jan. 31, 2019

(86) PCT No.: PCT/US2019/016006
§ 371 (c)(1),
(2) Date: Jul. 29, 2021

(87) PCT Pub. No.: WO2020/159506
PCT Pub. Date: Aug. 6, 2020

(65) Prior Publication Data
US 2022/0096287 A1    Mar. 31, 2022

(51) Int. Cl.
*A61F 13/15* (2006.01)
*A61F 13/84* (2006.01)
(Continued)

(52) U.S. Cl.
CPC ........ *A61F 13/84* (2013.01); *A61F 13/15617* (2013.01); *A61F 13/51113* (2013.01);
(Continued)

(58) Field of Classification Search
CPC ................. A61F 13/84; A61F 13/51113; A61F 13/15617; A61F 13/51401; A61L 15/28;
(Continued)

(56) References Cited

U.S. PATENT DOCUMENTS

| 8,481,299 B2 | 7/2013 | Gueniche |
| 8,951,775 B2 | 2/2015 | Castiel et al. |

(Continued)

FOREIGN PATENT DOCUMENTS

| CN | 101277684 A | 10/2008 |
| CN | 107072855 A | 8/2017 |

(Continued)

OTHER PUBLICATIONS

Tian, Yanjun et al., "Effect of nitrogen, carbon sources and agitation speed on acetoin production of Bacillus subtilis SF4-3", Electronic Journal of Biotechnology, Dec. 11, 2015, https://www.sciencedirect.com/science/article/pii/S0717345815001517.

(Continued)

*Primary Examiner* — Jacqueline F Stephens
(74) *Attorney, Agent, or Firm* — Kimberly-Clark Worldwide, Inc.

(57) ABSTRACT

Methods and products for maintaining a target pH range of an environment including at least one organism are provided. A method can include releasing a carbon source to the environment. A method can further include allowing the carbon source to be metabolized by the at least one organism and lower a pH of the environment. The method can also include releasing a nitrogen source to the environment. The method can additionally include allowing the nitrogen source to be metabolized by the at least one organism and increase the pH of the environment. The releasing of the carbon source to the environment and the releasing of the nitrogen source to the environment can be selectively timed (Continued)

to control the pH of the environment to the target pH range of the environment.

20 Claims, 5 Drawing Sheets

(51) Int. Cl.
    *A61F 13/511*     (2006.01)
    *A61L 15/28*     (2006.01)
    *A61L 15/46*     (2006.01)
    *A61F 13/514*     (2006.01)

(52) U.S. Cl.
    CPC ........ *A61F 13/51401* (2013.01); *A61L 15/28* (2013.01); *A61L 15/46* (2013.01); *A61L 2300/204* (2013.01); *A61L 2300/232* (2013.01)

(58) Field of Classification Search
    CPC ............... A61L 15/46; A61L 2300/204; A61L 2300/232
    USPC ........................................................ 604/359
    See application file for complete search history.

(56) References Cited

U.S. PATENT DOCUMENTS

| | | | |
|---|---|---|---|
| 9,738,870 B2 | 8/2017 | Whitlock et al. | |
| 2003/0096115 A1 | 5/2003 | Kozaki et al. | |
| 2006/0142711 A1* | 6/2006 | Underhill | A61F 13/15211 442/44 |
| 2008/0107699 A1 | 5/2008 | Spigelman et al. | |
| 2009/0317370 A1 | 12/2009 | Lang et al. | |
| 2010/0112054 A1 | 5/2010 | Peppas et al. | |
| 2015/0147768 A1 | 5/2015 | Chan et al. | |
| 2015/0202136 A1 | 7/2015 | Lanzalaco et al. | |
| 2017/0173091 A1 | 6/2017 | Lynch | |
| 2017/0281694 A1 | 10/2017 | Gantz et al. | |
| 2018/0296582 A1 | 10/2018 | von Maltzahn et al. | |
| 2019/0220611 A1 | 7/2019 | Nix | |

FOREIGN PATENT DOCUMENTS

| | | |
|---|---|---|
| JP | 2011019572 A | 2/2011 |
| WO | 2009008006 A2 | 1/2009 |
| WO | 2010133761 A1 | 11/2010 |
| WO | 2012175575 A2 | 12/2012 |
| WO | 2017035412 A1 | 3/2017 |

OTHER PUBLICATIONS

Van Beilen, Johan W.A et al., "Compailment-specific pH monitoring in Bacillus subtilis using fluorescent sensor proteins: a tool to analyze the antibacterial effect of weak organic acids", Frontiers in Microbiology, Jun. 18, 2013, https://www.ncbi.nlm.nih.gov/pmc/articles/PMC3685010/.

Karunai Selvi, B. et al., "Influence of different carbon and nitrogen sources on insoluble inorganic phosphate solubilization by Bacillus subtilis", International Journal of Advanced biological Research, 2012, http://scienceandnature.org/IJABR_Vol2(3)2012/IJABR_V2(3)11.pdf.

* cited by examiner

METHODS AND PRODUCTS FOR DYNAMIC CONTROL OF ENVIRONMENTS BY SELECTIVE METABOLIC FUNCTION OF MICROBES

BACKGROUND OF THE DISCLOSURE

Humans are colonized by microbes in the gastrointestinal tract, on the skin, and in other epithelial and tissue niches such as the nasal cavity, vaginal cavity, vulva, bladder, perineal, and perianal. In healthy persons a single local or tissue type may be inhabited by hundreds of different species of bacteria.

One of the major biophysical influencers of the human microbiome community structure is pH. For example, the pH of the skin can be altered by stratum corneum function as well as microflora metabolic function. Additionally, pH of the vaginal cavity, bladder, vulva, and nasal cavity is a function of both the microbes and host. The ability to maintain healthy pH on all body sites is key to skin and mucosal health. Maintaining a healthy pH can also lead to a balanced microbial flora in a human microbiome community. A healthy microbial flora provides the host with multiple benefits, including colonization resistance to a broad spectrum of pathogens, essential nutrient biosynthesis and absorption, and immune stimulation.

Therefore, there is a need for methods and products that will allow the human microflora to dynamically enhance pH balance of an environment of a subject.

SUMMARY OF THE DISCLOSURE

In one embodiment, a method for maintaining a target pH range of an environment including at least one organism is provided. The method can include releasing a carbon source to the environment. The method can further include allowing the carbon source to be metabolized by the at least one organism and lower a pH of the environment. The method can also include releasing a nitrogen source to the environment. The method can additionally include allowing the nitrogen source to be metabolized by the at least one organism and increase the pH of the environment. The releasing of the carbon source to the environment and the releasing of the nitrogen source to the environment can be selectively timed to control the pH of the environment to the target pH range of the environment.

In another embodiment, a product can include a first layer comprising one of a carbon source and a nitrogen source. The product can include a second layer comprising the other of the carbon source and the nitrogen source. The first layer and the second layer can be configured to be selectively available to an organism in an environment.

DEFINITIONS

As used herein, the term "inhibit" generally means to reduce by a measurable amount or to prevent entirely.

As used herein, the designation "wt/vol %" or "wt/vol" refers to the value obtained by dividing the weight of a substance (in grams) by the volume of the solution (in milliliters), and then multiplying by 100.

DETAILED DESCRIPTION OF THE DISCLOSURE

The present invention is related to methods and products that will allow the microflora in an environment to dynamically enhance pH balance of an environment through selective metabolic function of the microflora. The methods and products described herein can be utilized for maintaining pH of a variety of environments such as human microbiome communities, including, but not limited to: skin, gastrointestinal, nasal, vaginal cavity, vulva, bladder, perineal, and perianal. The products described herein can be utilized in a variety forms, as described further herein. For example, the products can be provided in capsule form that can be orally ingested or locally applied or placed in the target environment. Furthermore, the products can be provided as a film and/or as part of a substrate and applied or placed in the target environment.

Figure 1:
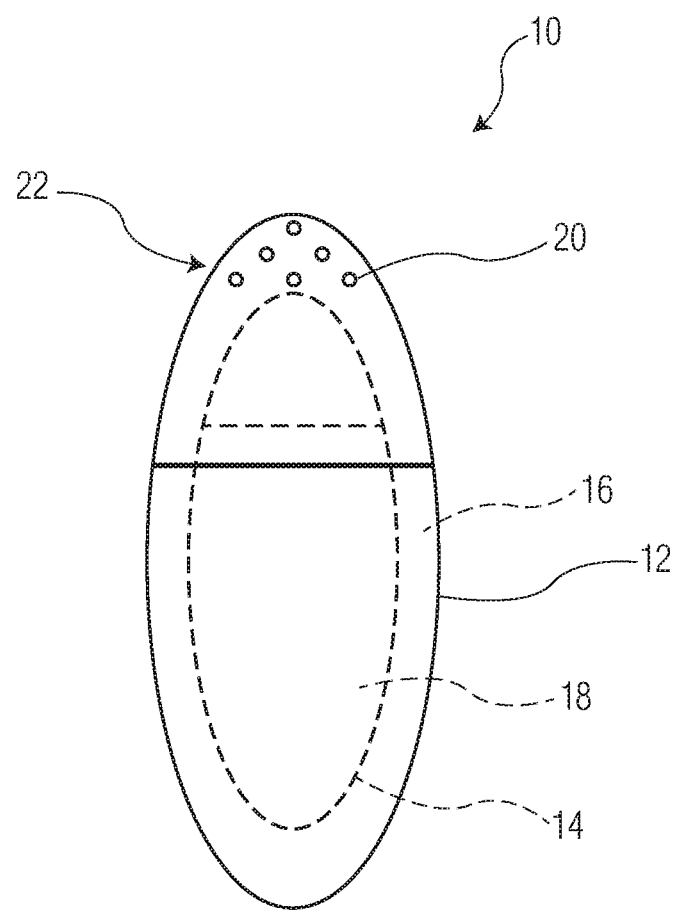
FIG. 1 illustrates a plan view of an exemplary embodiment of a product configured as a capsule including a carbon source and a nitrogen source in two layers.

In FIG. 1, a product 10 for dynamically controlling a pH of an environment is shown. The product 10 is configured as a capsule and includes a first layer 12 and a second layer 14. The first layer 12 can be configured as an outer layer for the capsule and the second layer 14 can be configured as an inner layer for the capsule. The first layer 12 can include a carbon source 16 or a nitrogen source 18. The second layer 14 can include a carbon source 16 or a nitrogen source 18, and preferably, includes the opposite source 16, 18 that is included in the first layer 12. For example, the first layer 12 can include a carbon source 16 and the second layer 14 can include a nitrogen source 18.

The first layer 12 and the second layer 14 are configured to be selectively available to an organism in the environment to be controlled. In the embodiment illustrated in FIG. 1, the first layer 12 covers the second layer 14, and as such, the first layer 12 can inhibit release and/or access of the components of the second layer 14 to the environment or organisms for at least an initial period of time. In some embodiments, the first layer 12 can inhibit release and/or access of the components of the second layer to the environment or organisms until the components of the first layer 12 are substantially metabolized by organisms in the environment or released into the environment. As illustrated in FIG. 1, the product 10 can include punctures 20 (only one labeled in FIG. 1 for clarity purposes) in one or more layers 12, 14 to assist in the release of the components of the layers 12, 14 and/or access to the layers 12, 14 to organisms in the environment. The capsule of FIG. 1 includes punctures 20 on the top portion 22 of the first layer 12. It is to be appreciated that punctures 20 can be included in alternative or additional locations on the first layer 12 and/or on other layers 14.

The carbon source 16 can be one or more of a variety of compounds that can provide carbon to an environment for organism(s) therein. The carbon source can be a fermentable carbon source that can include, but is not limited to: oligosaccharides, disaccharides, and monosaccharides such as glucose, fructose, maltose, isomaltose, sucrose, lactose, maltotriose, and galactose, trehalose, starch, dextrin, oligofrutose, and Galacto-oligosaccharides.

The nitrogen source 18 can be one or more of a variety of compounds that can provide nitrogen to an environment for organism(s) therein. Exemplary nitrogen sources 18 can include, but are not limited to: potassium nitrate, urea, ammonium chloride, ammonium sulfate, ammonium nitrate, and amino acids.

For experimentation of the dynamic control of the pH of an environment, an exemplary product 10 and bacteria cultures were prepared. An exemplary capsule similar to the product 10 illustrated in FIG. 1 was prepared with a targeted 10:1 molar ratio of the nitrogen source 18 in the second layer 14 to the carbon source 16 in the first layer 12. The nitrogen source 18 was $KNO_3$ (Mw 101.1 g/mol) and the carbon source 16 was glucose (Mw 181.1 g/mol). Both the glucose (CAS #50-99-7) and the potassium nitrate (CAS #7757791) was purchased from Acros Organics. In targeting the 10:1 molar ratio of the nitrogen source 18 to the carbon source 16, the exemplary embodiment included 50 mg glucose and 225 mg $KNO_3$ achieving a final concentration of 0.1% and 0.5% of glucose and $KNO_3$, respectively. A size #3 Capsugel® VCaps® Plus Hypromellose capsule (available from Lonza Company) was filled with the 50 mg of the glucose and was punctured seven times at the top portion 16 of the capsule with six punctures 20 being put around the side of the top portion 22 and one puncture 20 on the crown of the top portion 22. The punctures 20 were made with a 26⅜ G needle. A size #1 Capsugel® Plantcaps® Pullulan capsule (available from Lonza Company) was filled with the 225 mg of $KNO_3$ and was placed inside the size #3 Capsugel® VCaps® Plus capsule including the glucose. The capsule forming the second layer 14 and including the $KNO_3$ was not punctured. This product 10 was utilized in experiments described below.

The bacteria used in the experiments herein was *Bacillus subtilis*. The *Bacillus subtilis* 6051 was purchased from ATCC. Tryptin soy broth (TSB) was purchased from Fisher Scientific, as were the plates used for culturing. The TSB was modified per the ingredients and amounts as shown in Table 1 to provide modified TSB base media (mTSB). The ingredients of Table 1 were added to 1 L of water and the pH was adjusted to 6.5 and the media was autoclaved. The pH was measured using a Thermo Orion Versa Star purchased from Fisher Scientific.

TABLE 1 modified TSB base media

| Ingredient | Amount (g/L) |
| --- | --- |
| Casein peptone (pancreatic) | 17 |
| Sodium chloride | 5 |
| Soy peptone | 3 |

The *B. subtilis* was grown in 5 mL of TSB broth at 37° C. for 24 hours. One milliliter of each culture was washed twice with mTSB (Table 1) and re-suspended. 100 μL of washed bacteria was added to 100 mL of mTSB with and without addition of the product 10 capsules. Two product 10 capsules were used in each flask.

100 mL of mTSB was inoculated with 100 μL of washed *Bacillus subtilis* (approximately $10^6$ CFUs). Flasks were incubated for 24 hours at 37° C. with continuous pH measurements taken every 5 minutes.

Figure 2:
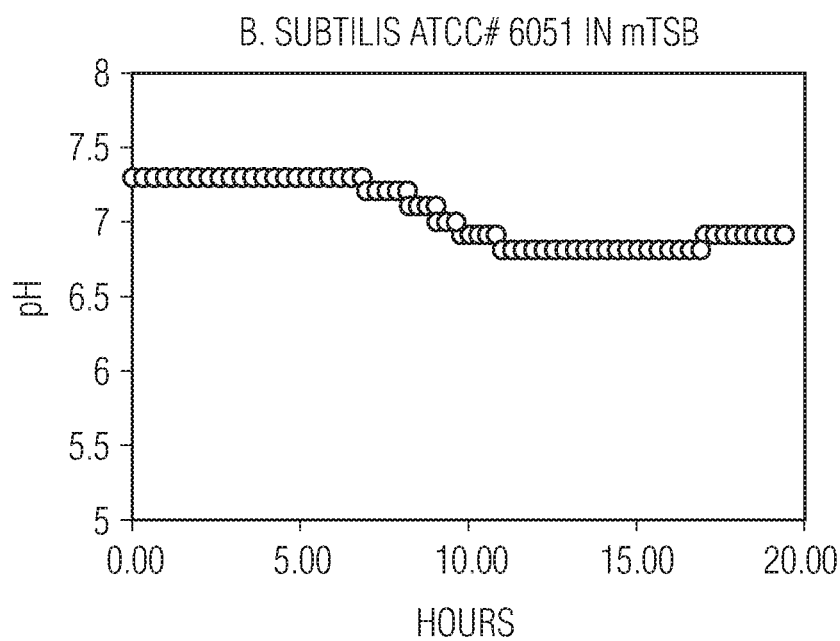
FIG. 2 illustrates a graph of pH against time for a sample of *Bacillus subtilis* in mTSB.

In a first aspect of the experiment, the *B. subtilis* was grown in mTSB without any product capsules 10. As illustrated in FIG. 2, the growth of *B. subtilis* resulted in a slight reduction of pH of about 0.5 over 20 hours.

Figure 3:
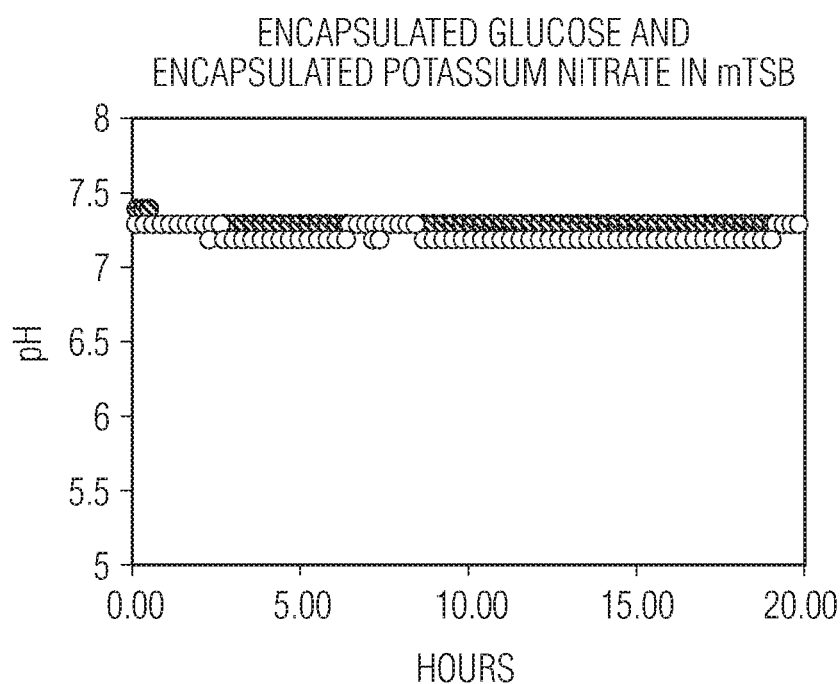
FIG. 3 illustrates a graph of pH against time for individual samples of encapsulated glucose in mTSB and encapsulated potassium nitrate in mTSB.

Turning to FIG. 3, the results from a control experiment are shown. 100 mg of the carbon source 16 of glucose and 550 mg of the nitrogen source 18 of potassium nitrate including glucose and potassium nitrate were included in their specific capsules as noted above, but were each incubated separately in mTSB without any *Bacillus subtilis*. As depicted in FIG. 3, the encapsulated glucose and the encapsulated potassium nitrate had little effect on the pH over the course of 20.0 hours in mTSB.

Figure 4:
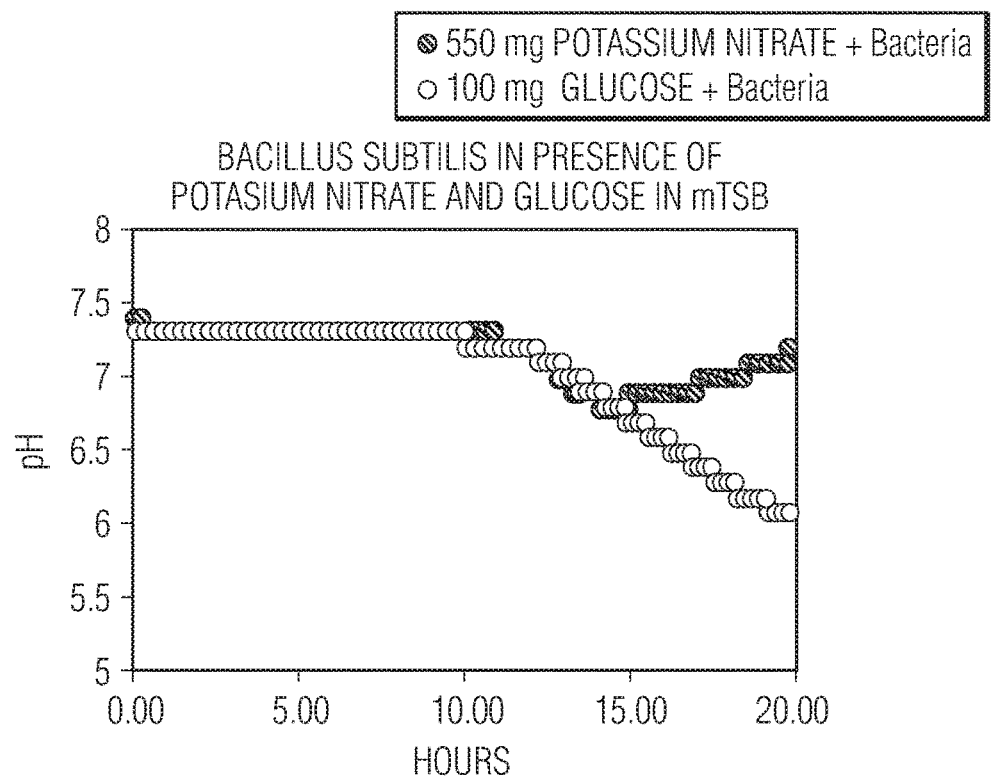
FIG. 4 illustrates a graph of pH against time for individual samples of encapsulated glucose in *Bacillus subtilis* and encapsulated potassium nitrate in *Bacillus subtilis*.

FIG. 4 depicts the results of providing 100 mg of encapsulated glucose in mTSB and *Bacillus subtilis* in one culture and providing 550 mg of encapsulated potassium nitrate in a separate culture. As demonstrated in FIG. 4, the addition of encapsulated glucose to mTSB in the presence of *B. subtilis* resulted in pH reduction of greater than 1.0 over the course of 20.0 hours of incubation. *B. subtilis* has the ability to metabolize glucose and produces acidic products, thus lowering the pH of the culture. In contrast, the addition of encapsulated potassium nitrate increased the pH by more than 0.5 after a slight decrease in pH of the culture.

Figure 5:
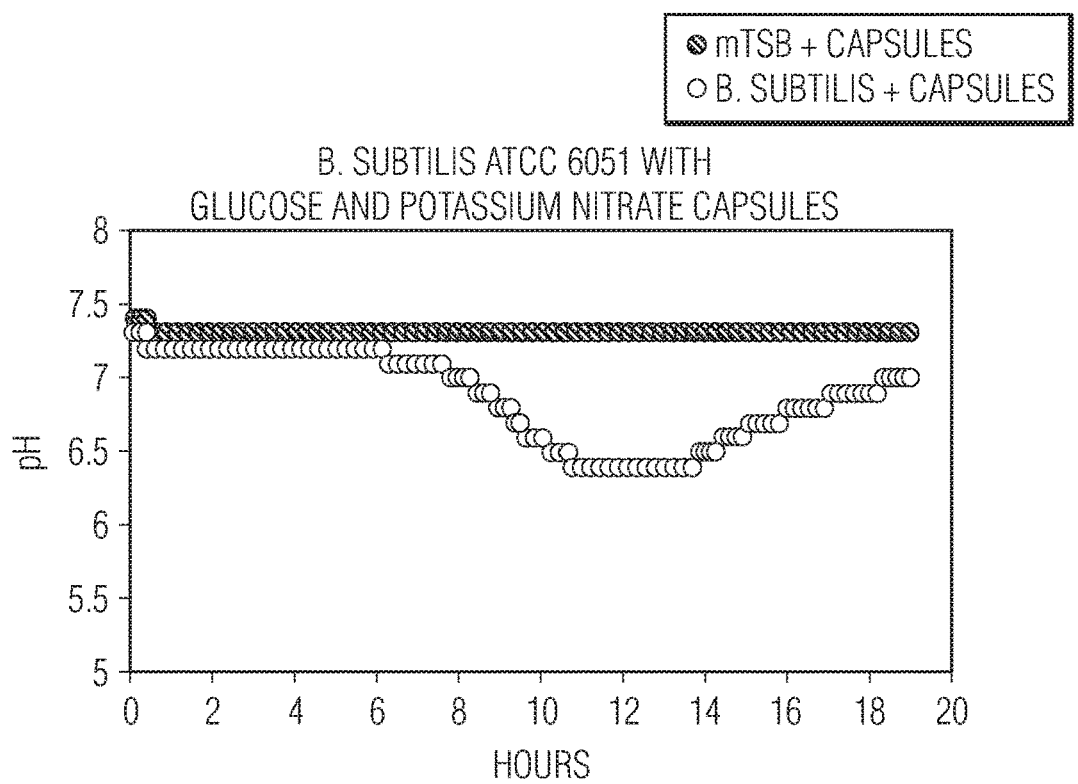
FIG. 5 illustrates a graph of pH against time for individual samples of encapsulated glucose and potassium nitrate incubated with *Bacillus subtilis* and without *Bacillus subtilis*.

The culturing of the multi-layered capsule described above including both 100 mg of a carbon source 16 of glucose in a first layer 12 and 500 mg of a nitrogen source 18 of potassium nitrate in a second layer 14 of two product 10 capsules incubated in mTSB and *Bacillus subtilis* is depicted in FIG. 5. As a control, two product 10 capsules were also incubated in mTSB without any *Bacillus subtilis*. As illustrated in FIG. 5, the culture not including any *Bacillus subtilis* kept an almost constant pH throughout the 20 hours of incubation. However, the culture including the two product 10 capsules and *Bacillus subtilis* in mTSB provided a substantial lower of pH from about 7.2 to about 6.4 from the time of about 6.0 hours to about 12.0 hours. Such lowering of the pH can be attributed to releasing the carbon source 16 of glucose in the first layer 12 to the *B. subtilis* such that the carbon source 16 can be metabolized by the *B. subtilis* providing acidic products from the metabolism. As also depicted in FIG. 5, the culture including the two product 10 capsules and *Bacillus subtilis* in mTSB provided a substantial raising of pH from about 6.4 to about 7.0 from the time of about 12.0 hours to about 18.0 hours. Such raising of the pH can be attributed to releasing the nitrogen source 18 of potassium nitrate in the second layer 14 to the *B. subtilis* such that the nitrogen source 16 can be metabolized by the *B. subtilis* providing basic products from the metabolism. Thus, the layered structure of the exemplary product 10 described herein has the ability to selectively time the releasing of or providing access to the carbon source 16 to the environment as well as the releasing of or providing access to the nitrogen source 18 to the environment in order to control the pH of the environment to a target pH range of the environment. In the example illustrated in FIG. 5, the target pH range of the environment was controlled between about 6.0 and 7.5, and more specifically, between about 6.4 and about 7.3.

This controlling of the pH of the environment within a target range can be accomplished by having such a layered carbon source 16 and nitrogen source 18 such that at least one of the carbon source 16 and the nitrogen source 18 is released before the other of the carbon source 16 and the nitrogen source 18. For example, in the embodiment described above, the carbon source 16 of glucose in the first layer 12 is released to the environment within the culture before the nitrogen source 18 of potassium nitrate in the second layer 14. Of course, it is to be appreciated that the nitrogen source 18 could be included in a first layer 12 and a carbon source 16 could be included in a second layer 14 in another embodiment. Such an alternative embodiment could first raise the pH through metabolism of the nitrogen source 18 and then later lower the pH through metabolism of the carbon source 16. Whether the carbon source 16 or nitrogen source 18 is included in the first layer 12 can depend on the potential environment that is being targeted and the pH of that environment.

Additionally, it is to be appreciated that different ratios and amounts of the carbon source 16 and the nitrogen source 18 other than exemplified in the experiments above may be employed to provide different control of the pH within a different target pH range.

Figure 6:
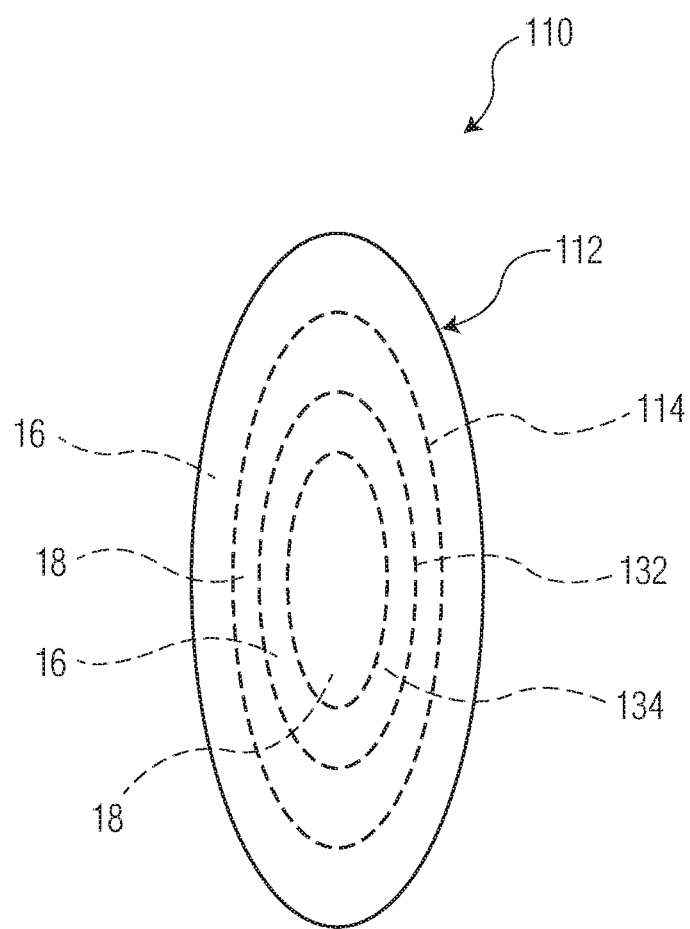
FIG. 6 illustrates a plan view of another embodiment of a product configured as a capsule including a carbon source and a nitrogen source in four layers.

To provide control of the pH of a target environment for a longer period of time and/or providing smaller step functions of lowering/raising or raising/lowering of the pH can also be accomplished. One such embodiment that can provide this functionality can be to provide a product 110 with more than one layer each of a carbon source 16 and a nitrogen source 18. One such example is depicted in the product 110 of FIG. 6 that is configured as a capsule with a first layer 112, a second layer 114, a third layer 132, and a fourth layer 134. The first layer 112 and the third layer 132 can be configured to include a carbon source 16. The second layer 114 and the fourth layer 134 can be configured to include a nitrogen source 18. In such a configuration, the product 110 can release a carbon source 16 as well as a nitrogen source 18 to the environment more than one time each, and in an alternating fashion. Of course, it is contemplated that the alternating layers 112, 114, 132, 134 can be configured such that the first layer 112 and the third layer 132 each include a nitrogen source 18 and the second layer 114 and the fourth layer 134 each include a carbon source 16.

In some embodiments, the first layer 112 can be configured substantially the same as the third layer 132. In some embodiments, the second layer 114 can be configured substantially the same as the fourth layer 134. As an example, the first layer 112 and the third layer 132 can be configured to include the substantially the same amounts of a carbon source 16. In some embodiments, the second layer 114 and the fourth layer 134 can be configured to include substantially the same amounts of a nitrogen source 18. In some embodiments, the first layer 112 and the third layer 132 can be configured such that they each include the same carbon source 16. In some embodiments, the second layer 114 and the fourth layer 134 can be configured such that they each include the same nitrogen source 18.

Figure 7:
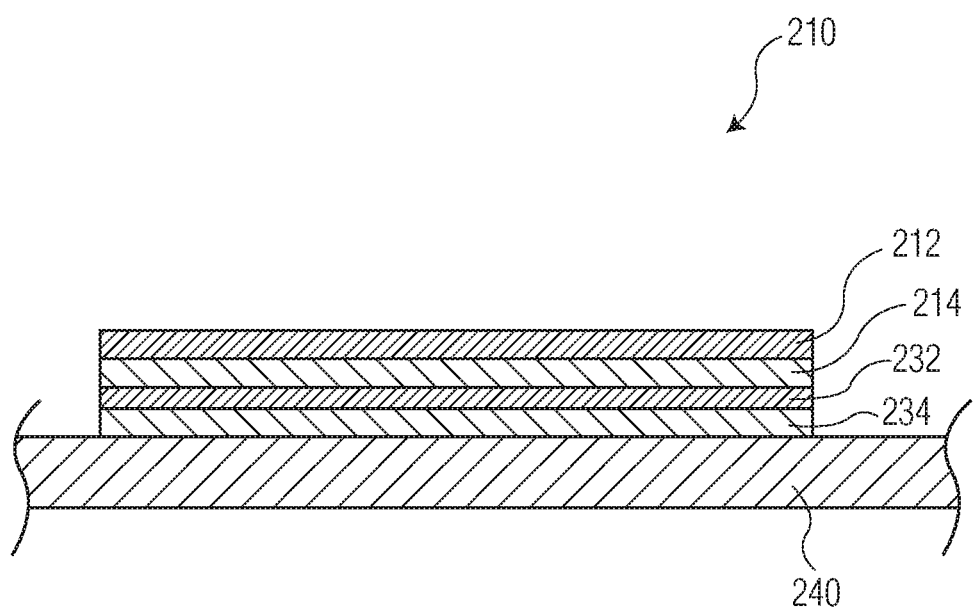
FIG. 7 illustrates a cross-sectional view of yet another embodiment of a product configured as a film including multiple layers deposited on a substrate.

Another alternative product 210 configuration is depicted in FIG. 7. FIG. 7 depicts that a product 210 can be configured as a film. In such a configuration of the product 210, the film may be independent of any other material or substrate, or as shown in FIG. 7, the film can be applied to or form part of a substrate 240. In some embodiments, the substrate 240 can form part of an absorbent article or wipe. The product 210 film can include a first layer 212, a second layer 214, a third layer 232, and a fourth layer 234. The product 210 film of FIG. 7 can be configured with similar options as described above with respect to the four-layer capsule product 110 described above and depicted in FIG. 6.

It is to be noted that any discussion of product 10 herein can be applied to the exemplary configurations of products 110, 210 as well, unless otherwise noted.

Alternative methods for releasing carbon sources 16 and nitrogen sources 18 to an environment can also be achieved utilizing cationic/anionic ratio and solubility (pKa dependency) of polymers. For example, a pH responsive polymer could be used as a vehicle for carbon and/or nitrogen sources to a target environment configured as a liquid media. Various functional groups could be covalently added to a polymer backbone to control solubility based on pKa values of the functional groups. Table 2 lists pKa values of potential exemplary functional groups and demonstrates that a wide range of pKa values exist for various molecules that could be added to a polymer backbone.

TABLE 2

Exemplary Functional Groups and pKa values

| Molecule | pKa (in water) |
| --- | --- |
| Carboxylic acid (R—COOH) | 4.76 |
| Methanol (MeOH) | 15.5 |
| Ammonia ($NH_3$) | 38 |
| Ammonium ($NH_4^+$) | 9.24 |
| Triethylamine ($Et_3$—$N^+$—H) | 10.6 |
| Acetamide ($CH_3$—$(CO)NH_2$) | 15.1 |

Combination of pH dependent cationic and anionic (e.g., acetic acid) polymers could be used to co-precipitate carbon and/or nitrogen compounds that can be electrostatically bonded to the polymer to create a product 10 in the configuration of a loaded film or as multi-layered coated particles (core-shell configuration). Exemplary Polymer Structure 1 depicts a cationic polymer comprised of polyacrylate backbone with an amine moiety where R1 and R2 is H or any aliphatic chain, such as, for example, $CH_3$, $CH_2CH_3$, and combinations thereof. R can be a spacer unit comprised of carbon atoms such as $CH_2$, $C_2H_4$, $C_3H_6$ and combinations thereof with a terminal quaternary amine that can provide a tunable moiety to achieve solubility in liquid media. The distance of the terminal quaternary amine from the polyacrylate backbone can be adjusted. The distance of the tertiary amine from the polyacrylate backbone can also be adjusted to be of varying carbon lengths. A ratio of x:y can represent the ratio between the cationic unit and a spacer unit/solubility unit. In some preferred embodiments, ratios of x:y can range from 1:5 to 5:1. By varying the ratio of x:y, the solubility of the polymer can be adjusted for the optimal cationic or anionic character of the compound, which would result in different pH dependencies. Polymer structure 1 could be protonated under acidic conditions and become a cation (tertiary amine). An anionic cargo molecule, such as a nitrate, could then be added to the polymer, which will be electrostatically bonded to the cation. When the pH of an environment increases (becomes more basic), deprotonation will occur leading to an overall neutral polymer. Being neutral, the polymer will precipitate while dissociating from the anionic compound thus releasing it into solution and providing access to the cargo molecule (such as a nitrate) that can provide a nitrogen source 18 for the environment. When an organism in the environment metabolizes the nitrogen source 18, the pH of the environment can be raised.

Exemplary Polymer Structure 1

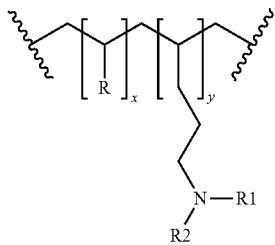

Another exemplary polymer structure is shown as Exemplary Polymer Structure 2. This polymer structure includes a polyacrylate backbone with an acetic acid moiety (distance of the acetic acid moiety from the polyacrylate backbone may be adjusted) and a spacer unit R. The spacer unit R can be H or another acetic acid moiety to adjust pH or solubility of the polymer. Similar to the Exemplary Polymer Structure 1, x and y can be modified to adjust the ratio between an anionic unit and a spacer unit/solubility unit. In some embodiments, ratios of x:y can range from 1:5 to 5:1. Exemplary Polymer Structure 2 could be modified to release a carbon source 16 or nitrogen source 18 by modifying the structure to dissolve and then dissociate within a liquid media, providing access to organisms in the environment to the carbon source 16 or nitrogen source 18. When an organism in the environment metabolizes the carbon source 16 or the nitrogen source 18, the pH of the environment can be modified as previously discussed.

Exemplary Polymer Structure 2

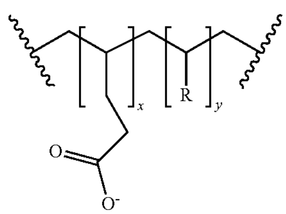

Exemplary Polymer Structure 3 depicts a cationic polymer comprised of polyacrylate backbone with moiety tertiary amine, a spacer unit (for example, $CH_2$, $C_2H_4$, $C_3H_6$, etc.), and a quaternary amine, and is shown on the left side of the reaction. The quaternary amine can provide solubility and the tertiary amine moiety provides the pH dependency response. With a pH decrease and introduction of a nitrogen source such as a nitrate (e.g., potassium nitrate), the tertiary amine moiety becomes protonated and the nitrite molecule can become associated with the quaternary amine by electrostatically binding to the quaternary amine. When the polymer dissolves in liquid media, the anionic cargo would dissociate from the polymer with a certain dissociation rate (could be instantaneous or slower). Another Exemplary Polymer Structure can add a cationic cargo and together the two polymer structures will provide their cargos (that can include a carbon source 16 and a nitrogen source 18) to the environment which will be metabolized by an organism and fluctuate the pH of the liquid media, which in turn affects the solubility of the polymers. Thus, the precipitation of a carbon source 16 and nitrogen source 18 can lead to controlling the pH of the target environment to a target pH range.

Exemplary Polymer Structure 3 in reaction

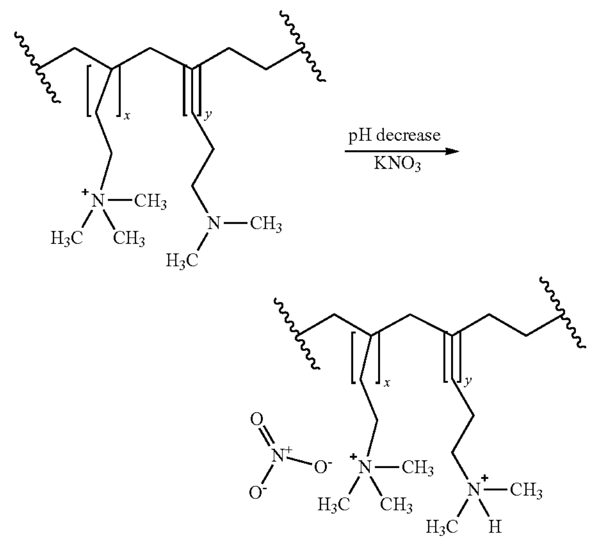

Carbon sources 16 and nitrogen sources 18 could be associated to a polymer via electrostatic interaction followed by co-precipitation to create a product 10 in the configuration of a loaded film or a spray and dry process depending on solubility to create a core-shell type structure, similar to the capsule structures discussed above. In the case of the latter, a solubilized polymer could be sprayed on a dried carbon and/or nitrogen source to create a coating layer. Once dried, this process could be repeated by spraying the now solubilized carbon and/or nitrogen source on the dry polymer.

Products 10 of the present disclosure can be in a variety of formats to be applied to a target environment of a user. As discussed above, products 10 can be in the form of a capsule configuration or a film configuration, for example. Depending on the target environment on the user, the product 10 can be ingested or locally applied to the target environment.

In some embodiments, the product 10 can be applied to or form part of a substrate, which in-turn may be used to apply the product 10 to the environment. Suitable substrates can include a web, such as a wet laid tissue web or air laid web, gauze, cotton swab, transdermal patch, container, or holder. Particularly preferred applicators include fibrous webs, including flushable and non-flushable cellulosic webs and nonwoven webs of synthetic fibrous material. Useful webs may be wet laid, air laid, meltblown, or spunbonded. Suitable synthetic fibrous material includes meltblown polyethylene, polypropylene, copolymers of polyethylene and polypropylene, bicomponent fibers including polyethylene or polypropylene, and the like. Useful nonwoven webs may be meltblown, coform, spunbond, airlaid, hydroentangled nonwovens, spunlace, bonded carded webs. In some embodiments, the substrate can be a component of or a portion of a component of an absorbent article (e.g., a diaper, training pant, tampon, fem pad, adult care garment and/or pant, etc.), a wipe, a tissue, or a towel.

Fibrous webs comprising a product 10 made according to the present disclosure can be incorporated into multi-ply products. For instance, in one aspect, a fibrous web made according to the present disclosure can be attached to one or more other fibrous webs to form a wiping product having desired characteristics. The other webs laminated to the fibrous web of the present disclosure can be, for instance, a wet-creped web, a calendered web, an embossed web, a through-air dried web, a creped through-air dried web, an uncreped through-air dried web, an airlaid web, and the like.

In other embodiments, the composition could be ingested or applied directly to the skin or other environment to dynamically enhance pH balance of an environment of a subject.

Embodiments

In view of the foregoing description and examples, the present disclosure provides the following embodiments.

Embodiment 1: A method for maintaining a target pH range of an environment including at least one organism; the method comprising: releasing a carbon source to the environment; allowing the carbon source to be metabolized by the at least one organism and lower a pH of the environment; releasing a nitrogen source to the environment; and allowing the nitrogen source to be metabolized by the at least one organism and increase the pH of the environment; wherein the releasing of the carbon source to the environment and the releasing of the nitrogen source to the environment are selectively timed to control the pH of the environment to the target pH range of the environment.

Embodiment 2: The method of embodiment 1, wherein the releasing of the carbon source to the environment and the releasing of the nitrogen source to the environment are selectively timed by layering the carbon source and the nitrogen source such that at least one of the carbon source and the nitrogen source is released before the other of the carbon source and the nitrogen source.

Embodiment 3: The method of embodiment 1 or 2, wherein the releasing of the carbon source to the environment occurs more than one time and the releasing of the nitrogen source occurs more than one time and the releasing of the carbon source and the releasing of the nitrogen source are provided in an alternating fashion.

Embodiment 4: The method of any one of the preceding embodiments, wherein the carbon source and the nitrogen source are configured in product comprising a first layer comprising one of the carbon source and the nitrogen source and a second layer comprising the other of the carbon source and the nitrogen source.

Embodiment 5: The method of embodiment 4, wherein the product is configured as a capsule.

Embodiment 6: The method of embodiment 4, wherein the product is configured as a film.

Embodiment 7: The method of any one of the preceding embodiments, wherein the releasing of the carbon source to the environment and the releasing of the nitrogen source to the environment are selectively timed by incorporating the carbon source and the nitrogen source in at least one pH responsive polymer.

Embodiment 8: The method of embodiment 7, wherein the at least one pH responsive polymer comprises a cationic polymer comprising a polyacrylate backbone with an-protonated amine moiety, a spacer unit, and a quaternary amine.

Embodiment 9: The method of any one of embodiments 1-6, wherein the releasing of the carbon source to the environment and the releasing of the nitrogen source to the environment are selectively timed by incorporating the carbon source and the nitrogen source in a combination of at least one pH dependent cationic polymer and at least one pH dependent anionic polymer.

Embodiment 10: The method of embodiment 9, wherein the at least one pH dependent cationic polymer comprises a polyacrylate backbone with at least two amine moieties, a first amine moiety including a secondary nitrogen or a tertiary nitrogen with any aliphatic chain, and a second amine moiety including a terminal quaternary amine.

Embodiment 11: The method of embodiment 9 or 10, wherein the at least one pH dependent anionic polymer comprises a polyacrylate backbone and at least one acetic acid moiety, the at least one acetic acid moiety being separated from the polyacrylate backbone by a spacer unit.

Embodiment 12: The method of any one of the preceding embodiments, wherein the environment comprises a human microbiome community selected from the group consisting of: skin, gastro-intestinal, nasal, vaginal cavity, vulva, bladder, perineal, and perianal.

Embodiment 13: A product comprising: a first layer comprising one of a carbon source and a nitrogen source; a second layer comprising the other of the carbon source and the nitrogen source; wherein the first layer and the second layer are configured to be selectively available to an organism in an environment.

Embodiment 14: The product of embodiment 13, wherein the product is configured as a capsule.

Embodiment 15: The product of embodiment 14, wherein the first layer provides an outer layer for the capsule and the second layer provides an inner layer for the capsule.

Embodiment 16: The product of embodiment 14, wherein the first layer provides the carbon source and the second layer provides the nitrogen source.

Embodiment 17: The product of any one of embodiments 14-16, wherein the product further comprises: a third layer being substantially the same as the first layer; and a fourth layer being substantially the same as the second layer.

Embodiment 18: The product of any one of embodiments 14-17, wherein the capsule comprises punctures.

Embodiment 19: The product of embodiment 13, wherein the product is a film.

Embodiment 20: The product of embodiment 19, wherein the film is applied to or forms part of a substrate.

What is claimed is:

1. A method for maintaining a target pH range of an environment including at least one organism; the method comprising:
    releasing a carbon source to the environment;
    allowing the carbon source to be metabolized by the at least one organism and lower a pH of the environment;
    releasing a nitrogen source to the environment; and
    allowing the nitrogen source to be metabolized by the at least one organism and increase the pH of the environment;
    wherein the releasing of the carbon source to the environment and the releasing of the nitrogen source to the environment are selectively timed to control the pH of the environment to the target pH range of the environment.

2. The method of claim 1, wherein the releasing of the carbon source to the environment and the releasing of the nitrogen source to the environment are selectively timed by layering the carbon source and the nitrogen source such that at least one of the carbon source and the nitrogen source is released before the other of the carbon source and the nitrogen source.

3. The method of claim 1, wherein the releasing of the carbon source to the environment occurs more than one time and the releasing of the nitrogen source occurs more than one time and the releasing of the carbon source and the releasing of the nitrogen source are provided in an alternating fashion.

4. The method of claim 1, wherein the carbon source and the nitrogen source are configured in product comprising a first layer comprising one of the carbon source and the nitrogen source and a second layer comprising the other of the carbon source and the nitrogen source.

5. The method of claim 4, wherein the product is configured as a capsule.

6. The method of claim 4, wherein the product is configured as a film.

7. The method of claim 1, wherein the releasing of the carbon source to the environment and the releasing of the nitrogen source to the environment are selectively timed by incorporating the carbon source and the nitrogen source in at least one pH responsive polymer.

8. The method of claim 7, wherein the at least one pH responsive polymer comprises a cationic polymer comprising a polyacrylate backbone with an-protonated amine moiety, a spacer unit, and a quaternary amine.

9. The method of claim 1, wherein the releasing of the carbon source to the environment and the releasing of the nitrogen source to the environment are selectively timed by incorporating the carbon source and the nitrogen source in a combination of at least one pH dependent cationic polymer and at least one pH dependent anionic polymer.

10. The method of claim 9, wherein the at least one pH dependent cationic polymer comprises a polyacrylate backbone with at least two amine moieties, a first amine moiety including a secondary nitrogen or a tertiary nitrogen with any aliphatic chain, and a second amine moiety including a terminal quaternary amine.

11. The method of claim 9, wherein the at least one pH dependent anionic polymer comprises a polyacrylate backbone and at least one acetic acid moiety, the at least one acetic acid moiety being separated from the polyacrylate backbone by a spacer unit.

12. The method of claim 1, wherein the environment comprises a human microbiome community selected from the group consisting of: skin, gastro-intestinal, nasal, vaginal cavity, vulva, bladder, perineal, and perianal.

13. A product comprising:
a first layer comprising one of a carbon source and a nitrogen source;
a second layer comprising the other of the carbon source and the nitrogen source;
wherein the first layer and the second layer are configured to be selectively available to an organism in an environment.

14. The product of claim 13, wherein the product is configured as a capsule.

15. The product of claim 14, wherein the first layer provides an outer layer for the capsule and the second layer provides an inner layer for the capsule.

16. The product of claim 14, wherein the first layer provides the carbon source and the second layer provides the nitrogen source.

17. The product of claim 14, wherein the product further comprises:
a third layer being substantially the same as the first layer; and
a fourth layer being substantially the same as the second layer.

18. The product of claim 14, wherein the capsule comprises punctures.

19. The product of claim 13, wherein the product is a film.

20. The product of claim 19, wherein the film is applied to or forms part of a substrate.

* * * * *